United States Patent
Takeda et al.

(10) Patent No.: US 10,370,369 B2
(45) Date of Patent: Aug. 6, 2019

(54) ACID ADDITION SALT OF 3-AMINOQUINUCLIDINE WHICH DOES NOT EXHIBIT DELIQUESCENCE

(71) Applicant: YUKI GOSEI KOGYO CO. LTD., Tokyo (JP)

(72) Inventors: Yukiko Takeda, Tokyo (JP); Tetsuji Noda, Tokyo (JP)

(73) Assignee: YUKI GOSEI KOGYO CO. LTD., Tokyo (JP)

(*) Notice: Subject to any disclaimer, the term of this patent is extended or adjusted under 35 U.S.C. 154(b) by 0 days.

(21) Appl. No.: 15/561,262

(22) PCT Filed: Mar. 31, 2016

(86) PCT No.: PCT/JP2016/060746
§ 371 (c)(1),
(2) Date: Sep. 25, 2017

(87) PCT Pub. No.: WO2016/159268
PCT Pub. Date: Oct. 6, 2016

(65) Prior Publication Data
US 2018/0118736 A1    May 3, 2018

(30) Foreign Application Priority Data

Mar. 31, 2015 (JP) ................ 2015-073920
Mar. 31, 2015 (JP) ................ 2015-073921
Mar. 31, 2015 (JP) ................ 2015-073922

(51) Int. Cl.
| | |
|---|---|
| C07D 453/02 | (2006.01) |
| C07C 55/07 | (2006.01) |
| C07C 57/15 | (2006.01) |
| C07C 57/34 | (2006.01) |
| C07C 309/25 | (2006.01) |
| C07C 309/30 | (2006.01) |

(52) U.S. Cl.
CPC ............ *C07D 453/02* (2013.01); *C07C 55/07* (2013.01); *C07C 57/15* (2013.01); *C07C 57/34* (2013.01); *C07C 309/25* (2013.01); *C07C 309/30* (2013.01)

(58) Field of Classification Search
CPC .................................................... C07D 453/02
USPC ......................................................... 546/133
See application file for complete search history.

(56) References Cited

U.S. PATENT DOCUMENTS

| | | | | |
|---|---|---|---|---|
| 5,017,580 | A | * 5/1991 | Naylor | ................ A61K 31/435 |
| | | | | 514/299 |
| 6,894,042 | B2 | * 5/2005 | Walker | ................ C07D 471/08 |
| | | | | 514/212.05 |
| 2003/0232853 | A1 | 12/2003 | Walker et al. | |
| 2004/0224976 | A1 | 11/2004 | Walker et al. | |

FOREIGN PATENT DOCUMENTS

| | | | | |
|---|---|---|---|---|
| CN | 101613349 | | * 12/2009 | ........... C07D 453/02 |
| CN | 101613349 | A | 12/2009 | |
| JP | 02-256616 | A | 10/1990 | |
| JP | 2005-523287 | A | 8/2005 | |

OTHER PUBLICATIONS

Patent Cooperation Treaty, International Search Report for PCT/JP2016/060746 dated Jun. 28, 2016, 2 pages.
Patent Cooperation Treaty, Written Opinion of the International Searching Authority for PCT/JP2016/060746 dated Jun. 28, 2016, 4 pages.
EPO Form 1507S—Extended European Search Report, dated Aug. 8, 2018, for corresponding European Application No. 16773148.8.
"3-Amino-chinuclidin-dihydrochlorid" In: "Laborchemikalien und analytische Reagenzien", 2005, Fluka/Riedel de Haen, p. 95.

* cited by examiner

*Primary Examiner* — Nizal S Chandrakumar
(74) *Attorney, Agent, or Firm* — Heslin Rothenberg Farley & Mesiti P.C.; Adolph Bohnstedt

(57) ABSTRACT

A novel acid addition salt of 3-aminoquinuclidine, which is an industrially useful compound as an intermediate of medicines and does not exhibit deliquescence, is provided.
In particular, an acid addition salt of 3-aminoquinuclidine selected from the group consisting of racemic 3-aminoquinuclidine, (R)-3-aminoquinuclidine, and (S)-3-aminoquinuclidine, and acid selected from the group consisting of phosphoric acid, sulfuric acid, fumaric acid, terephthalic acid, oxalic acid, p-toluenesulfonic acid, (±)-10-camphorsulfonic acid, and (−)-10-camphorsulfonic acid, is provided.

3 Claims, No Drawings

ACID ADDITION SALT OF 3-AMINOQUINUCLIDINE WHICH DOES NOT EXHIBIT DELIQUESCENCE

CROSS REFERENCE TO RELATED APPLICATIONS

This application is a national stage filing under section 371 of International Application No. PCT/JP2016/060746, filed on 31 Mar. 2016, published in Japanese on 6 Oct. 2016, as WO2016/159268 A1 and which claims priority to Japanese Application Nos. JP 2015-073920 filed 31 Mar. 2015, JP 2015-073921 filed 31 Mar. 2015, and JP 2015-073922 filed 31 Mar. 2015, the entire disclosure of these applications being hereby incorporated herein by reference.

TECHNICAL FIELD

The present invention relates to an acid addition salt of 3-aminoquinuclidine.

BACKGROUND ART 3-aminoquinuclidine dihydrochloride is used as an intermediate of various fine chemicals as well as an intermediate of medicines and agricultural chemicals, and is a useful compound industrially. In connection to this, 3-aminoquinuclidine according to an embodiment of the present invention includes a racemic form of 3-aminoquinuclidine (hereinafter sometimes referred to as racemic 3-aminoquinuclidine), (R)-3-aminoquinuclidine, and (S)-3-aminoquinuclidine.

SUMMARY OF INVENTION

Technical Problem 3-aminoquinuclidine dihydrochloride is used as an intermediate of medicines. However, it has a high hygroscopicity and deliquescence, and thus it is very difficult to handle. Further, there is a problem, for example, in that absorbed water has some effect on a manufacturing process of medicine. However, an acid addition salt of racemic 3-aminoquinuclidine, an acid addition salt of (R)-3-aminoquinuclidine, and an acid addition salt of (S)-3-aminoquinuclidine in which the hygroscopicity and deliquescence are improved, have not been reported until now.

Accordingly, an object of the present invention is to provide 3-aminoquinuclidine, which has an excellent handleability.

Solution to Problem

The present inventors have conducted intensive studies into 3-aminoquinuclidine having an excellent handleability. As a result, the present inventors have prepared acid addition salts of racemic 3-aminoquinuclidine, (R)-3-aminoquinuclidine, or (S)-3-aminoquinuclidine, and specific acids, and have found novel acid addition salts of 3-aminoquinuclidine which have an excellent non-hygroscopicity and does not exhibit deliquescence. Then, the present inventors completed the present invention.

Accordingly, the present invention relates to:

[I] an acid addition salt of 3-aminoquinuclidine selected from the group consisting of racemic 3-aminoquinuclidine, (R)-3-aminoquinuclidine, and (S)-3-aminoquinuclidine, and acid selected from the group consisting of phosphoric acid, sulfuric acid, fumaric acid, terephthalic acid, oxalic acid, p-toluenesulfonic acid, (±)-10-camphorsulfonic acid, and (−)-10-camphorsulfonic acid, wherein the acid addition salt does not exhibit deliquescence,

[II] the acid addition salt of item [I], of racemic 3-aminoquinuclidine and acid selected from the group consisting of phosphoric acid, fumaric acid, terephthalic acid, oxalic acid, p-toluenesulfonic acid, and (±)-10-camphorsulfonic acid, wherein the acid addition salt does not exhibit deliquescence,

[III] the acid addition salt of item [I] or [II], selected from the group consisting of

[1] racemic 3-aminoquinuclidine.sesquiphosphate,
[2] racemic 3-aminoquinuclidine.monofumarate,
[3] racemic 3-aminoquinuclidine.monoterephthalate,
[4] racemic 3-aminoquinuclidine.monooxalate,
[5] racemic 3-aminoquinuclidine.mono-p-toluenesulfonate, and
[6] racemic 3-aminoquinuclidine.mono-(±)-10-camphorsulfonate,

[IV] The acid addition salt of item [I], of (R)-3-aminoquinuclidine and acid selected from the group consisting of phosphoric acid, sulfuric acid, fumaric acid, terephthalic acid, oxalic acid, p-toluenesulfonic acid, and (−)-10-camphorsulfonic acid, wherein the acid addition salt does not exhibit deliquescence,

[V] the acid addition salt of item [I] or [IV], selected from the group consisting of

[1] (R)-3-aminoquinuclidine.sesquiphosphate,
[2] (R)-3-aminoquinuclidine.monosulfate,
[3] (R)-3-aminoquinuclidine.monofumarate,
[4] (R)-3-aminoquinuclidine.monoterephthalate,
[5] (R)-3-aminoquinuclidine.monooxalate,
[6] (R)-3-aminoquinuclidine.mono-p-toluenesulfonate, and
[7] (R)-3-aminoquinuclidine.mono-(−)-10-camphorsulfonate,

[VI] the acid addition salt of item [I], of (S)-3-aminoquinuclidine and acid selected from the group consisting of phosphoric acid, sulfuric acid, fumaric acid, terephthalic acid, oxalic acid, and p-toluenesulfonic acid, wherein the acid addition salt does not exhibit deliquescence,

[VII] The acid addition salt of item [I] or [VI], selected from the group consisting of

[1] (S)-3-aminoquinuclidine.sesquiphosphate,
[2] (S)-3-aminoquinuclidine.monosulfate,
[3] (S)-3-aminoquinuclidine.monofumarate,
[4] (S)-3-aminoquinuclidine.monoterephthalate,
[5] (S)-3-aminoquinuclidine.monooxalate, and
[6] (S)-3-aminoquinuclidine.mono-p-toluenesulfonate,

[VIII] a method for preserving 3-aminoquinuclidine, comprising preserving 3-aminoquinuclidine as an acid addition salt of 3-aminoquinuclidine selected from the group consisting of racemic 3-aminoquinuclidine, (R)-3-aminoquinuclidine, and (S)-3-aminoquinuclidine and acid selected from the group consisting of phosphoric acid, sulfuric acid, fumaric acid, terephthalic acid, oxalic acid, p-toluenesulfonic acid, (±)-10-camphorsulfonic acid, and (−)-10-camphorsulfonic acid,

[IX] the method for preserving 3-aminoquinuclidine of item [VIII], comprising preserving racemic 3-aminoquinuclidine as an acid addition salt of racemic 3-aminoquinuclidine and acid selected from the group consisting of phosphoric acid, fumaric acid, terephthalic acid, oxalic acid, p-toluenesulfonic acid, and (±)-10-camphorsulfonic acid,

[X] the method for preserving 3-aminoquinuclidine of item [VIII] or [IX], wherein the acid addition salt is selected from the group consisting of

[1] racemic 3-aminoquinuclidine.sesquiphosphate,
[2] racemic 3-aminoquinuclidine.monofumarate,
[3] racemic 3-aminoquinuclidine.monoterephthalate,
[4] racemic 3-aminoquinuclidine.monooxalate,
[5] racemic 3-aminoquinuclidine.mono-p-toluenesulfonate, and
[6] racemic 3-aminoquinuclidine.mono-(±)-10-camphorsulfonate,
[XI] the method for preserving 3-aminoquinuclidine of item [VIII],comprising preserving (R)-3-aminoquinuclidine as an acid addition salt of (R)-3-aminoquinuclidine and acid selected from the group consisting of phosphoric acid, sulfuric acid, fumaric acid, terephthalic acid, oxalic acid, p-toluenesulfonic acid, and (−)-10-camphorsulfonic acid,
[XII] the method for preserving 3-aminoquinuclidine of item[VIII] or [XI], wherein the acid addition salt is selected from the group consisting of
[1] (R)-3-aminoquinuclidine.sesquiphosphate,
[2] (R)-3-aminoquinuclidine.monosulfate,
[3] (R)-3-aminoquinuclidine.monofumarate,
[4] (R)-3-aminoquinuclidine.monoterephthalate,
[5] (R)-3-aminoquinuclidine.monooxalate,
[6] (R)-3-aminoquinuclidine.mono-p-toluenesulfonate, and
[7] (R)-3-aminoquinuclidine.mono(−)-10-camphorsulfonate,
[XIII] the method for preserving 3-aminoquinuclidine of item [VIII], comprising preserving (S)-3-aminoquinuclidine as an acid addition salt of (S)-3-aminoquinuclidine and acid selected from the group consisting of phosphoric acid, sulfuric acid, fumaric acid, terephthalic acid, oxalic acid, and p-toluenesulfonic acid, and
[XIV] the method for preserving 3-aminoquinuclidine of item [VIII] or [XIII], wherein the acid addition salt is selected from the group consisting of
[1] (S)-3-aminoquinuclidine.sesquiphosphate,
[2] (S)-3-aminoquinuclidine.monosulfate,
[3] (S)-3-aminoquinuclidine.monofumarate,
[4] (S)-3-aminoquinuclidine.monoterephthalate,
[5] (S)-3-aminoquinuclidine.monooxalate, and
[6] (S)-3-aminoquinuclidine.mono-p-toluenesulfonate.

In this regard, an acid addition salt of racemic 3-aminoquinuclidine, an acid addition salt of (R)-3-aminoquinuclidine, and an acid addition salt of (S)-3-aminoquinuclidine in which the hygroscopicity and deliquescence are improved, have not been reported until now.

Advantageous Effects of Invention

According to an embodiment of the present invention, novel acid addition salts of racemic 3-aminoquinuclidine, novel acid addition salts of (R)-3-aminoquinuclidine, and novel acid addition salts of (S)-3-aminoquinuclidine, which have an excellent non-hygroscopicity and does not exhibit deliquescence, can be provided. Further, according to an embodiment of the present invention, a novel method for preserving racemic 3-aminoquinuclidine, a novel method for preserving (R)-3-aminoquinuclidine, and a novel method for preserving (S)-3-aminoquinuclidine can be provided.

DESCRIPTION OF EMBODIMENTS

The present invention will be described in detail hereinafter.
[I] to [VII] Acid Addition Salt of 3-Aminoquinuclidine An acid addition salt of 3-aminoquinuclidine, which does not exhibit deliquescence, according to an embodiment of the present invention is prepared from 3-aminoquinuclidine selected from the group consisting of racemic 3-aminoquinuclidine, (R)-3-aminoquinuclidine, and (S)-3-aminoquinuclidine, and acid selected from the group consisting of phosphoric acid, sulfuric acid, fumaric acid, terephthalic acid, oxalic acid, p-toluenesulfonic acid, (±)-10-camphorsulfonic acid, and (−)-10-camphorsulfonic acid.

For example, the acid addition salt of racemic 3-aminoquinuclidine, acid addition salt of (R)-3-aminoquinuclidine, or acid addition salt of (S)-3-aminoquinuclidine can be prepared as follows.

An acid being used as a salt, or a solution containing the acid, is added to a solution containing free racemic 3-aminoquinuclidine, free (R)-3-aminoquinuclidine, or free (S)-3-aminoquinuclidine, at an equivalent weight range of 0.5 to 2.0 with respect to racemic 3-aminoquinuclidine, (R)-3-aminoquinuclidine, or (S)-3-aminoquinuclidine. Then, a crystalline acid addition salt can be precipitated by stirring or allowing to stand at room temperature or cooling temperature. A procedure for charging the above acid is not limited. That is to say, the solution containing free racemic 3-aminoquinuclidine, free (R)-3-aminoquinuclidine, or free (S)-3-aminoquinuclidine may be added to the acid being used as a salt, or the solution containing the acid. A preferable acid usage is around an amount of equivalent weight of the acid addition salt which is formed. If a large excessive acid is added, a yield thereof is reduced conversely.

Then, the precipitated crystal is filtered to obtain the crystal, and the acid addition salt of racemic 3-aminoquinuclidine, acid addition salt of (R)-3-aminoquinuclidine, or acid addition salt of (S)-3-aminoquinuclidine can be obtained by drying the crystal.

The acid addition salt of racemic 3-aminoquinuclidine, which does not exhibit deliquescence, according to an embodiment of the present invention, is preferably acid addition salts of racemic 3-aminoquinuclidine and acid selected from the group consisting of phosphoric acid, fumaric acid, terephthalic acid, oxalic acid, p-toluenesulfonic acid, and (±)-10-camphorsulfonic acid. These acid addition salts, which are not described in any reference, are novel compounds. Further, the acid addition salt of racemic 3-aminoquinuclidine which does not exhibit deliquescence, more preferably includes [1]racemic 3-aminoquinuclidine.sesquiphosphate $(C_7H_{14}N_2 \cdot 1.5H_3PO_4)$, [2] racemic 3-aminoquinuclidine.monofumarate $(C_7H_{14}N_2 \cdot C_4H_4O_4)$, [3] racemic 3-aminoquinuclidine.monoterephthalate $(C_7H_{14}N_2 \cdot C_8H_6O_4)$, [4] racemic 3-aminoquinuclidine.monooxalate $(C_7H_{14}N_2 \cdot H_2C_2O_4)$, [5] racemic 3-aminoquinuclidine.mono-p-toluenesulfonate $(C_7H_{14}N_2 \cdot C_7H_8O_3S)$, and [6] racemic 3-aminoquinuclidine.mono-(±)-10-camphorsulfonate $(C_7H_{14}N_2C_{10}H_{16}O_4S)$.

The acid addition salt of (R)-3-aminoquinuclidine, which does not exhibit deliquescence, according to an embodiment of the present invention, is preferably acid addition salts of (R)-3-aminoquinuclidine and acid selected from the group consisting of phosphoric acid, sulfuric acid, fumaric acid, terephthalic acid, oxalic acid, p-toluenesulfonic acid, and (−)-10-camphorsulfonic acid. These acid addition salts, which are not described in any reference, are novel compounds. Further, the acid addition salt of (R)-3-aminoquinuclidine which does not exhibit deliquescence, more preferably includes [1] (R)-3-aminoquinuclidine.sesquiphosphate $(C_7H_{14}N_2 \cdot 1.5H_3PO_4)$, [2] (R)-3-aminoquinuclidine.monosulfate $(C_7H_{14}N_2 \cdot H_2SO_4)$, [3] (R)-3-aminoquinuclidine.monofumarate $(C_7H_{14}N_2 \cdot C_4H_4O_4)$, [4] (R)-3-aminoquinuclidine.monoterephthalate $(C_7H_{14}N_2 \cdot C_8H_6O_4)$, [5] (R)-3- aminoquinuclidine.monooxalate (C₇H₁₄N₂.H₂C₂O₄), [6] (R)-3-aminoquinuclidine.mono-p-toluenesulfonate (C₇H₁₄N₂.C₇H₈O₃S), and [7] (R)-3-aminoquinuclidine.mono-(−)-10-camphorsulfonate (C₇H₁₄N₂.C₁₀H₁₆O₄S).

The acid addition salt of (S)-3-aminoquinuclidine, which does not exhibit deliquescence, according to an embodiment of the present invention, is preferably acid addition salts of (S)-3-aminoquinuclidine and acid selected from the group consisting of phosphoric acid, sulfuric acid, fumaric acid, terephthalic acid, oxalic acid, and p-toluenesulfonic acid. These acid addition salts, which are not described in any reference, are novel compounds. Further, the acid addition salt of (S)-3-aminoquinuclidine, which does not exhibit deliquescence, more preferably includes [1] (S)-3-aminoquinuclidine.sesquiphosphate (C₇H₁₄N₂.1.5H₃PO₄), [2] (S)-3-aminoquinuclidine.monosulfate (C₇H₁₄N₂.H₂SO₄), [3] (S)-3-aminoquinuclidine.monofumarate (C₇H₁₄N₂.C₄H₄O₄), [4] (S)-3-aminoquinuclidine.monoterephthalate (C₇H₁₄N₂.C₈H₆O₄), [5] (S)-3-aminoquinuclidine.monooxalate (C₇H₁₄N₂.H₂C₂O₄), and [6] (S)-3-aminoquinuclidine.mono-p-toluenesulfonate (C₇H₁₄N₂.C₇H₈O₃S).

In the present invention, as a solvent for preparing the solution containing free racemic 3-aminoquinuclidine, free (R)-3-aminoquinuclidine, or free (S)-3-aminoquinuclidine, or for preparing the solution containing acid, there may be mentioned water, ketone(s), alcohol(s), hydrocarbon(s), ether(s), chloromethane(s), nitrile(s), and the like. Specifically, there may be mentioned water, acetone, methyl ethyl ketone, methanol, ethanol, propanol, butanol, hexane, heptane, toluene, xylene, diethyl ether, tetrahydrofuran, chloroform, dichloromethane, acetonitrile, and the like.

[VIII] to [XIV] Method for Preserving 3-Aminoquinuclidine

A method for preserving 3-aminoquinuclidine according to an embodiment of the present invention includes preserving 3-aminoquinuclidine as an acid addition salt of 3-aminoquinuclidine selected from the group consisting of racemic 3-aminoquinuclidine, (R)-3-aminoquinuclidine, and (S)-3-aminoquinuclidine and acid selected from the group consisting of phosphoric acid, sulfuric acid, fumaric acid, terephthalic acid, oxalic acid, p-toluenesulfonic acid, (±)-10-camphorsulfonic acid, and (−)-10-camphorsulfonic acid Preferably, the method for preserving racemic 3-aminoquinuclidine according to an embodiment of the present invention is includes preserving racemic 3-aminoquinuclidine as an acid addition salt of racemic 3-aminoquinuclidine and acid selected from the group consisting of phosphoric acid, fumaric acid, terephthalic acid, oxalic acid, p-toluenesulfonic acid, and (±)-10-camphorsulfonic acid. In the method for preserving racemic 3-aminoquinuclidine according to an embodiment of the present invention, a more preferable acid addition salt is [1] racemic 3-aminoquinuclidine sesquiphosphate, [2] racemic 3-aminoquinuclidine.monofumarate, [3] racemic 3-aminoquinuclidine.monoterephthalate, [4] racemic 3-aminoquinuclidine.monooxalate, [5] racemic 3-aminoquinuclidine.mono-p-toluenesulfonate, and [6] racemic 3-aminoquinuclidine.mono-(±)-10-camphorsulfonate.

Racemic 3-aminoquinuclidine preserved in the preserving method according to an embodiment of the present invention is a compound of the formula (1):

[Chem. 1]

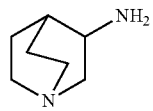

(1)

The racemic 3-aminoquinuclidine is prepared as the acid addition salt of racemic 3-aminoquinuclidine and phosphoric acid, fumaric acid, terephthalic acid, oxalic acid, p-toluenesulfonic acid or (±)-10-camphorsulfonic acid, according to the method described in the above item of "[I] to [VII] Acid addition salt of 3-aminoquinuclidine", and then preserved. According to the method for preserving racemic 3-aminoquinuclidine according to an embodiment of the present invention, racemic 3-aminoquinuclidine exhibits an excellent non-hygroscopicity, and the deliquescence of racemic 3-aminoquinuclidine can be suppressed.

Preferably, the method for preserving (R)-3-aminoquinuclidine according to an embodiment of the present invention includes preserving (R)-3-aminoquinuclidine as an acid addition salt of (R)-3-aminoquinuclidine and acid selected from the group consisting of phosphoric acid, sulfuric acid, fumaric acid, terephthalic acid, oxalic acid, p-toluenesulfonic acid, and (−)-10-camphorsulfonic acid. In the method for preserving (R)-3-aminoquinuclidine according to an embodiment of the present invention, a more preferable acid addition salt is [1] (R)-3-aminoquinuclidine.sesquiphosphate, [2] (R)-3-aminoquinuclidine.monosulfate, [3] (R)-3-aminoquinuclidine.monofumarate, [4] (R)-3-aminoquinuclidine.monoterephthalate, [5] (R)-3-aminoquinuclidine.monooxalate, [6] (R)-3-aminoquinuclidine.mono-p-toluenesulfonate, and [7] (R)-3-aminoquinuclidine.mono-(−)-10-camphorsulfonate.

(R)-3-aminoquinuclidine preserved in the preserving method according to an embodiment of the present invention is a compound of the formula (2):

[Chem. 2]

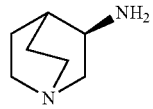

(2)

The (R)-3-aminoquinuclidine is prepared as the acid addition salt of (R)-3-aminoquinuclidine and phosphoric acid, sulfuric acid, fumaric acid, terephthalic acid, oxalic acid, p-toluenesulfonic acid, or (−)-10-camphorsulfonic acid, according to the method described in the above item of "[I] to [VII] Acid addition salt of 3-aminoquinuclidine", and then preserved. According to the method for preserving (R)-3-aminoquinuclidine according to an embodiment of the present invention, (R)-3-aminoquinuclidine exhibits an excellent non-hygroscopicity, and the deliquescence of (R)-3-aminoquinuclidine can be suppressed.

Preferably, the method for preserving (S)-3-aminoquinuclidine according to an embodiment of the present invention includes preserving (S)-3-aminoquinuclidine as an acid addition salt of (S)-3-aminoquinuclidine and acid selected from the group consisting of phosphoric acid, sulfuric acid, fumaric acid, terephthalic acid, oxalic acid, and p-toluenesulfonic acid. In the method for preserving (S)-3-aminoquinuclidine according to an embodiment of the present invention, a more preferable acid addition salt is [1] (S)-3- aminoquinuclidine sesquiphosphate, [2] (S)-3-aminoquinuclidine.monosulfate, [3] (S)-3-aminoquinuclidine.monofumarate, [4] (S)-3-aminoquinuclidine.monoterephthalate, [5](S)-3-aminoquinuclidine.monooxalate, and [6] (S)-3-aminoquinuclidine.mono-p-toluenesulfonate.

(S)-3-aminoquinuclidine preserved in the preserving method according to an embodiment of the present invention is a compound of the formula (3):

[Chem. 3]

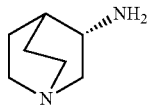

(\32)

The (S)-3-aminoquinuclidine is prepared as the acid addition salt of (S)-3-aminoquinuclidine and phosphoric acid, sulfuric acid, fumaric acid, terephthalic acid, oxalic acid, or p-toluenesulfonic acid, according to the method described in the above item of "[I] to ~[VII] Acid addition salt of 3-aminoquinuclidine", and then preserved. According to the method for preserving (S)-3-aminoquinuclidine according to an embodiment of the present invention, (S)-3-aminoquinuclidine exhibits an excellent non-hygroscopicity, and the deliquescence of (S)-3-aminoquinuclidine can be suppressed.

A temperature of the preserving method of the present invention is not particularly limited, but for example, 0° C. to 80° C., preferably 0° C. to 50° C. Further, a humidity of the preserving method of the present invention is not particularly limited, but for example, 0 to 80%, preferably 0 to 50%, which is a low humidity.

EXAMPLES

The present invention will now be further illustrated by, but is by no means limited to, the following Examples.

In connection with this, the title compounds in the following examples, referential examples, and comparative examples are described as a non-solvate.

However, each of the salts sometimes may be a form of solvate depending on a condition of preparation.

As a racemic 3-aminoquinuclidine.dihydrochloride, the reagent purchased from Tokyo Chemical Industry Co., Ltd was used as it is.

Referential Example 1: Synthesis of racemic 3-aminoquinuclidine

Racemic 3-aminoquinuclidine was obtained by neutralization-extracting racemic 3-aminoquinuclidine dihydrochloride and concentrating the same in accordance with a method described in Japanese Patent No. 4779248.

Example 1: Synthesis of racemic 3-aminoquinuclidine.sesquiphosphate

Methanol solution (33.27 g) containing racemic 3-aminoquinuclidine (3.13 g: 24.8 mmol) was charged into a 50 mL-flask equipped with a mechanical stirrer, a thermometer, and a cooling line, and phosphoric acid (85% in water) (4.31 g: 37.4 mmol) was added thereto while stirring at room temperature. Precipitated crystals were filtered, and then dried under reduced pressure at 60° C., to obtain racemic 3-aminoquinuclidine-1.5 phosphate (6.17 g: 22.6 mmol, yield=91%) as a white crystal.

1H-NMR ($D_2O$, ppm): 1.82-1.99 (4H, m), 2.24-2.26 (1H, m), 3.07-3.27 (5H, m), 3.59-3.65 (1H, m), 3.71-3.74 (1H, m)

Endothermic peak top temperature in DSC: 158° C., 226° C., 278° C.

Elemental analysis: $C_7H_{14}N_2 \cdot 1.5H_3PO_4$

Theoretical value: P, 17.01% Actual measured value: P, 16.5%

Example 2: Synthesis of racemic 3-aminoquinuclidine.monofumarate

Methanol suspension (20.73 g) containing fumaric acid (2.74 g: 23.6 mmol) was charged into a 50 mL-flask equipped with a mechanical stirrer, a thermometer, and a cooling line, and methanol solution (9.00 g) containing racemic 3-aminoquinuclidine (3.00 g: 23.8 mmol) was added thereto while stirring at room temperature. Precipitated crystals were filtered, and then dried under reduced pressure at 60° C., to obtain racemic 3-aminoquinuclidine.monofumarate (5.56 g: 22.9 mmol, yield=97%) as a white crystal.

1H-NMR ($D_2O$, ppm): 1.82-2.01 (4H, m), 2.26-2.30 (1H, m), 3.09-3.27 (5H, m), 3.62-3.68 (1H, m), 3.75-3.80 (1H, m) 6.35 (2H, s)

Endothermic peak top temperature in DSC: 207° C.

Elemental analysis: $C_7H_{14}N_2 \cdot C_4H_4O_4$

Theoretical value: C, 54.53%, H, 7.49%, N, 11.56%

Actual measured value: C, 54.7%, H, 7.4%, N, 11.8%

Example 3: Synthesis of racemic 3-aminoquinuclidine.monoterephthalate

Methanol suspension (21.96 g) containing terephthalic acid (3.95 g:23.8 mmol) was charged into a 50 mL-flask equipped with a mechanical stirrer, a thermometer, and a cooling line, and methanol solution (9.06 g) containing racemic 3-aminoquinuclidine (3.05 g: 24.1 mmol) was added thereto while stirring at room temperature. Precipitated crystals were filtered, and then dried under reduced pressure at 60° C., to obtain racemic 3-aminoquinuclidine.monoterephthalate (6.75 g: 23.1 mmol, yield=96%) as a white crystal.

1H-NMR ($D_2O$, ppm): 1.76-1.95 (4H, m), 2.20-2.24 (1H, m), 3.03-3.25 (5H, m), 3.56-3.63 (1H, m), 3.70-3.74 (1H, m), 7.71 (4H, s)

Endothermic peak top temperature in DSC: 277° C.

Elemental analysis: $C_7H_{14}N_2 \cdot C_8H_6O_4$

Theoretical value: C, 61.63%, H, 6.90%, N, 9.58%

Actual measured value: C, 61.6%, H, 6.9%, N, 9.7%

Example 4: Synthesis of racemic 3-aminoquinuclidine.monooxalate

Methanol solution (18.00 g) containing racemic 3-aminoquinuclidine (3.00 g:23.8 mmol) was charged into a 50 mL-flask equipped with a mechanical stirrer, a thermometer, and a cooling line, and methanol solution (11.15 g) containing oxalic acid (2.14 g: 23.8 mmol) was added thereto while stirring at room temperature. Precipitated crystals were filtered, and then dried under reduced pressure at 60° C., to obtain racemic 3-aminoquinuclidine.monooxalate (4.55 g: 21.0 mmol, yield=89%) as a white crystal.

1H-NMR ($D_2O$, ppm): 1.82-2.01 (4H, m), 2.26-2.30 (1H, m), 3.09-3.27 (5H, m), 3.61-3.68 (1H, m), 3.74-3.80 (1H, m)

Endothermic peak top temperature in DSC: 280° C.
Elemental analysis: $C_7H_{14}N_2 \cdot C_2H_2O_4$
Theoretical value: C, 49.99%, H, 7.46%, N, 12.96%
Actual measured value: C, 49.8%, H, 7.4%, N, 12.9%

Example 5: Synthesis of racemic 3-aminoquinuclidine.mono-p-toluenesulfonate 2-propanol solution (12.12 g) containing racemic 3-aminoquinuclidine (3.02 g: 23.9 mmol) was charged into a 50 mL-flask equipped with a mechanical stirrer, a thermometer, and a cooling line, and 2-propanol solution (19.48 g) containing p-toluenesulfonic acid monohydrate (4.53 g: 23.8 mmol) was added thereto while stirring at room temperature. Precipitated crystals were filtered, and then dried under reduced pressure at 60° C., to obtain racemic 3-aminoquinuclidine.mono-p-toluenesulfonate (6.76 g: 22.7 mmol, yield=95%) as a white crystal.
1H-NMR (D$_2$O, ppm): 1.60-1.97 (5H, m), 2.23 (3H, s), 2.64-2.68 (1H, m), 2.91-3.11 (4H, m), 3.20-3.24 (1H, m), 3.34-3.40 (1H, m), 7.21 (2H, d, J=8 Hz), 7.53 (2H, d, J=8 Hz)
Endothermic peak top temperature in DSC: 198° C.
Elemental analysis: $C_7H_{14}N_2 \cdot C_7H_8O_3S$
Theoretical value: C, 56.35%, H, 7.43%, N, 9.39%, S 10.74%
Actual measured value: C, 56.4%, H, 7.5%, N, 9.3%, S 10.2%

Example 6: Synthesis of racemic 3-aminoquinuclidine.mono-(±)-10-camphorsulfonate 2-propanol solution (18.00 g) containing racemic 3-aminoquinuclidine (3.00 g:23.8 mmol) was charged into a 50 mL-flask equipped with a mechanical stirrer, a thermometer, and a cooling line, and 2-propanol solution (15.51 g) containing (±)-10-camphorsulfonic acid (5.52 g: 23.8 mmol) was added thereto while stirring at room temperature. Precipitated crystals were filtered, and then dried under reduced pressure at 60° C., to obtain racemic 3-aminoquinuclidine.mono-(±)-10-camphorsulfonate (6.63 g: 18.5 mmol, yield=78%) as a white crystal.
1H-NMR (D$_2$O, ppm): 0.67 (3H, s), 0.88 (3H, s), 1.27-1.34 (1H, m), 1.44-1.51 (1H, m), 1.64-2.01 (8H, m), 2.21-2.30 (2H, m), 2.65-2.70 (1H, m), 2.70 (1H, d, J=14.9 Hz), 2.96-3.10 (4H, m), 3.12 (1H, d, J=14.9 Hz), 3.22-3.27 (1H, m), 3.35-3.42 (1H, m)
Endothermic peak top temperature in DSC: 168° C., 195° C.
Elemental analysis: $C_7H_{14}N_2 \cdot C_{10}H_{16}O_4S$
Theoretical value: C, 56.96%, H, 8.44%, N, 7.81%, S 8.94%
Actual measured value: C, 57.0%, H, 8.3%, N, 7.6%, S 8.6%

Comparative Example 1: Synthesis of racemic 3-aminoquinuclidine-dihydrobromide 2-propanol solution (31.14 g) containing racemic 3-aminoquinuclidine (4.96 g: 39.3 mmol) was charged into a 50 mL-flask equipped with a mechanical stirrer, a thermometer, and a cooling line, and 47% hydrobromic acid (13.70 g: 79.6 mmol) was added thereto while stirring at room temperature. Precipitated crystals were filtered, and then dried under reduced pressure at 60° C., to obtain racemic 3-aminoquinuclidine-dihydrobromide (6.87 g: 23.8 mmol, yield=61%) as a white crystal.
1H-NMR (D$_2$O, ppm): 1.86-2.05 (4H, m), 2.30-2.34 (1H, m), 3.13-3.31 (5H, m), 3.67-3.73 (1H, m), 3.80-3.86 (1H, m)
Endothermic peak top temperature in DSC: 248° C.

<<Comparative Example 2: Synthesis of racemic 3-aminoquinuclidine.monosulfate

Ethanol solution (26.97 g) containing racemic 3-aminoquinuclidine (2.97 g: 23.5 mmol) was charged into a 50 mL-flask equipped with a mechanical stirrer, a thermometer, and a cooling line, and 95% sulfuric acid (2.42 g: 23.4 mmol) was added thereto while stirring at room temperature. Precipitated crystals were filtered, and then dried under reduced pressure at 60° C., to obtain racemic 3-aminoquinuclidine.monosulfate (4.31 g: 19.2 mmol, yield=82%) as a white crystal.
1H-NMR (D$_2$O, ppm): 1.85-2.04 (4H, m), 2.30-2.34 (1H, m), 3.14-3.43 (5H, m), 3.65-3.72 (1H, m), 3.80-3.84 (1H, m)
Endothermic peak top temperature in DSC: 271° C., 294° C.

Comparative Example 3: Synthesis of racemic 3-aminoquinuclidine.dinitrate 2-propanol solution (45.10 g) containing racemic 3-aminoquinuclidine (5.00 g (39.6 mmol) was charged into a 100 mL-flask equipped with a mechanical stirrer, a thermometer, and a cooling line, and 70% nitric acid (7.27 g: 79.6 mmol) was added thereto while stirring at room temperature. Precipitated crystals were filtered, and then dried under reduced pressure at 60° C., to obtain racemic 3-aminoquinuclidine.dinitrate (9.51 g: 37.7 mmol, yield=95%) as a white crystal.
1H-NMR (D$_2$O, ppm): 1.85-2.04 (4H, m), 2.30-2.34 (1H, m), 3.12-3.30 (5H, m), 3.66-3.72 (1H, m), 3.80-3.84 (1H, m)
Endothermic peak top temperature in DSC: 248° C.

Comparative Example 4: Synthesis of racemic 3-aminoquinuclidine.diacetate

Toluene solution (55.77 g) containing racemic 3-aminoquinuclidine (5.56 g: 44.1 mmol) was charged into a 100 mL-flask equipped with a mechanical stirrer, a thermometer, and a cooling line, and acetic acid (5.33 g: 88.8 mmol) was added thereto while stirring at room temperature. Precipitated crystals were filtered, and then dried under reduced pressure at 60° C., to obtain racemic 3-aminoquinuclidine.diacetate (4.41 g: 39.0 mmol, yield=89%) as a white crystal.
1H-NMR (D$_2$O, ppm): 1.74 (6H, s), 1.81-2.01 (4H, m), 2.23-2.28 (1H, m), 3.08-3.26 (5H, m), 3.60-3.66 (1H, m), 3.71-3.76 (1H, m)
Endothermic peak top temperature in DSC: 120° C., 152° C.

Comparative Example 5: Synthesis of racemic 3-aminoquinuclidine.monopropionate

Toluene solution (21.00 g) containing racemic 3-aminoquinuclidine (3.00 g: 23.8 mmol) was charged into a 50 mL-flask equipped with a mechanical stirrer, a thermometer, and a cooling line, and propionic acid (1.75 g: 23.6 mmol) was added thereto while stirring at room temperature. Precipitated crystals were filtered, and then dried under reduced pressure at 60° C., to obtain racemic 3-aminoquinuclidine.monopropionate (2.17 g: 10.8 mmol, yield=46%) as a white crystal.

1H-NMR (D$_2$O, ppm): 0.88 (3H, t, J=7.83 Hz), 1.61-1.99 (5H, m), 2.00 (2H, q, J=7.83 Hz), 2.64-2.69 (1H, m), 2.92-3.07 (4H, m), 3.21-3.26 (1H, m), 3.34-3.40 (1H, m)

Endothermic peak top temperature in DSC: 109° C., 160° C.

Comparative Example 6: Synthesis of racemic 3-aminoquinuclidine.dibenzoate 2-propanol solution (20.82 g) containing benzoic acid (5.81 g: 47.6 mmol) was charged into a 50 mL-flask equipped with a mechanical stirrer, a thermometer, and a cooling line, and 2-propanol solution (9.01 g) containing racemic 3-aminoquinuclidine (3.01 g: 23.9 mmol) was added thereto while stirring at room temperature. Precipitated crystals were filtered, and then dried under reduced pressure at 60° C., to obtain racemic 3-aminoquinuclidine.dibenzoate (7.53 g: 20.3 mmol, yield=85%) as a white crystal.

1H-NMR (D$_2$O, ppm): 1.77-1.97 (4H, m), 2.20-2.24 (1H, m), 3.04-3.24 (5H, m), 3.57-3.63 (1H, m), 3.68-3.72 (1H, m), 7.28-7.32 (4H, m), 7.35-7.40 (2H, m), 7.68-7.71 (4H, m)

Endothermic peak top temperature in DSC: 140° C., 224° C.

Comparative Example 7: Synthesis of racemic 3-aminoquinuclidine.monomaleate 2-propanol solution (17.76 g) containing maleic acid (2.76 g: 23.8 mmol) was charged into a 50 mL-flask equipped with a mechanical stirrer, a thermometer, and a cooling line, and 2-propanol solution (11.99 g) containing racemic 3-aminoquinuclidine (2.99 g: 23.7 mmol) was added thereto while stirring at room temperature. Precipitated crystals were filtered, and then dried under reduced pressure at 60° C., to obtain racemic 3-aminoquinuclidine.monomaleate (4.97 g: 13.9 mmol, yield=63%) as a white crystal.

1H-NMR (D$_2$O, ppm): 1.81-2.01 (4H, m), 2.22-2.26 (1H, m), 3.07-3.27 (5H, m), 3.58-3.64 (1H, m), 3.69-3.74 (1H, m), 5.89 (2H, s)

Endothermic peak top temperature in DSC: 135° C., 186° C.

Comparative Example 8: Synthesis of racemic 3-aminoquinuclidine.2/3 citrate 2-propanol solution (16.02 g) containing racemic 3-aminoquinuclidine (4.02 g: 31.9 mmol) was charged into a 50 mL-flask equipped with a mechanical stirrer, a thermometer, and a cooling line, and isopropanol solution (16.12 g) containing citric acid (anhydrous) (4.04 g: 21.0 mmol) was added thereto while stirring at room temperature. Precipitated crystals were filtered, and then dried under reduced pressure at 60° C., to obtain racemic 3-aminoquinuclidine.2/3citrate (7.30 g: 28.7 mmol, yield=90%) as a white crystal.

1H-NMR (D$_2$O, ppm): 1.82-2.01 (4H, m), 2.62-2.30 (1H, m), 2.41 (2/3H, d, J=14.9 Hz), 2.52 (2/3H, d, J=14.9 Hz), 3.09-3.30 (5H, m), 3.61-3.67 (1H, m), 3.76-3.79 (1H, m)

Endothermic peak top temperature in DSC: 194° C.

Comparative Example 9: Synthesis of racemic 3-aminoquinuclidine.monomesylate 2-propanol solution (27.11 g) containing racemic 3-aminoquinuclidine (2.97 g: 23.5 mmol) was charged into a 50 mL-flask equipped with a mechanical stirrer, a thermometer, and a cooling line, and mesylic acid (2.28 g: 23.7 mmol) was added thereto while stirring at room temperature. Precipitated crystals were filtered, and then dried under reduced pressure at 60° C., to obtain racemic 3-aminoquinuclidine.monomesylate (4.46 g: 20.1 mmol, yield=85%) as a white crystal.

1H-NMR (D$_2$O, ppm): 1.62-1.99 (5H, m), 2.64 (3H, s), 2.64-2.70 (1H, m), 2.93-3.12 (4H, m), 3.23-3.27 (1H, m), 3.35-3.41 (1H, m)

Endothermic peak top temperature in DSC: 156° C.

Experimental Example 1: Deliquescence Test racemic 3-aminoquinuclidine.dihydrochloride of reagent, and the acid addition salts (about 0.5 g) of racemic 3-aminoquinuclidine obtained in Examples 1 to 6 and Comparative Examples 1 to 9 were allowed to stand for 1 hour, under the condition of 25 to 27° C., and a humidity of 76 to 82%, and a deliquescence was observed by a visual evaluation. The results are shown in Table 1.

TABLE 1

| | Salt | Deliquescence |
|---|---|---|
| Example 1 | Sesquiphosphate | Not deliquesce |
| Example 2 | Monofumarate | Not deliquesce |
| Example 3 | Monoterephthalate | Not deliquesce |
| Example 4 | Monooxalate | Not deliquesce |
| Example 5 | Mono-p-toluenesulfonate | Not deliquesce |
| Example 6 | Mono-(±)-10-camphorsulfonate | Not deliquesce |
| Reagent | Dihydrochloride | Immediately deliquesce |
| Comparative Example 1 | Dihydrobromide | Gradually deliquesce |
| Comparative Example 2 | Monosulfate | Gradually deliquesce |
| Comparative Example 3 | Dinitrate | Gradually deliquesce |
| Comparative Example 4 | Diacetate | Immediately deliquesce |
| Comparative Example 5 | Monopropionate | Immediately deliquesce |
| Comparative Example 6 | Dibenzoate | Gradually deliquesce |
| Comparative Example 7 | Monomaleate | Gradually deliquesce |
| Comparative Example 8 | ⅔ citrate | Immediately deliquesce |
| Comparative Example 9 | Monomesylate | Gradually deliquesce |

Referential Example 2: Synthesis of (R)-3-aminoquinuclidine.dihydrochloride (R)-3-aminoquinuclidine.dihydrochloride was obtained by subjecting a starting material i.e., 3-quinuclidine.monohydrochloride to some sequential reactions in accordance with a method described in Synth. Commun., 22 (13), 1895-1911 (1992).

Referential Example 3: Synthesis of (R)-3-aminoquinuclidine (R)-3-aminoquinuclidine was obtained by neutralization-extracting (R)-3-aminoquinuclidine dihydrochloride and concentrating the same in accordance with a method described in Japanese Patent No. 4779248.

Example 7: Synthesis of (R)-3-aminoquinuclidine.sesquiphosphate

Methanol solution (27.04 g) containing (R)-3-aminoquinuclidine (3.04 g: 24.1 mmol) was charged into a 50 mL-flask equipped with a magnetic stirrer, a thermometer, and a cooling line, and phosphoric acid (85% in water) (4.15 g: 36.0 mmol) was added thereto while stirring at room temperature. Precipitated crystals were filtered, and then dried under reduced pressure at 65° C., to obtain (R)-3-aminoquinuclidine.sesquiphosphate (6.67 g: 24.4 mmol, yield=101%) as a white crystal.

1H-NMR (D$_2$O, ppm): 1.82-2.02 (4H, m), 2.24-2.28 (1H, m), 3.08-3.29 (5H, m), 3.60-3.66 (1H, m), 3.71-3.75 (1H, m)

Endothermic peak top temperature in DSC: 190° C., 230° C., 279° C.

Elemental analysis: C$_7$H$_{14}$N$_2$.1.5H$_3$PO$_4$
Theoretical value: P, 17.01%
Actual measured value: P, 17.0%

Example 8: Synthesis of (R)-3-aminoquinuclidine.monosulfate

Toluene solution (22.84 g) containing (R)-3-aminoquinuclidine (3.50 g:27.7 mmol) was charged into a 50 mL-flask equipped with a mechanical stirrer, a thermometer, and a cooling line, and 95% sulfuric acid (2.87 g: 27.8 mmol) was added thereto while stirring on ice. Precipitated crystals were filtered, and then dried under reduced pressure at 60° C., to obtain (R)-3-aminoquinuclidine.monosulfate (4.85 g: 21.6 mmol, yield=78%) as a white crystal.

1H-NMR (D$_2$O, ppm): 1.83-2.01 (4H, m) 2.29-2.33 (1H, m), 3.10-3.33 (5H, m), 3.64-3.70 (1H, m), 3.78-3.81 (1H, m)

Endothermic peak top temperature in DSC: 108° C., 175° C., 286° C.

Elemental analysis: C$_7$H$_{14}$N$_2$.H$_2$SO$_4$
Theoretical value: C, 37.49%, H, 7.19%, N, 12.49%, S 14.29%
Actual measured value: C, 36.5%, H, 7.1%, N, 12.3%, S 14.4%

Example 9: Synthesis of (R)-3-aminoquinuclidine.monofumarate

Methanol solution (29.92 g) containing (R)-3-aminoquinuclidine (4.98 g: 39.5 mmol) was charged into a 50 mL-flask equipped with a mechanical stirrer, a thermometer, and a cooling line, and methanol suspension (14.61 g) containing fumaric acid (4.60 g: 39.6 mmol) was added thereto while stirring at room temperature. Precipitated crystals were filtered, and then dried under reduced pressure at 60° C., to obtain (R)-3-aminoquinuclidine.monofumarate (9.01 g (37.2 mmol, yield=94%) as a white crystal.

1H-NMR (D$_2$O, ppm): 1.83-2.02 (4H, m), 2.28-2.30 (1H, m), 3.10-3.29 (5H, m), 3.63-3.69 (1H, m), 3.76-3.81 (1H, m), 6.36 (2H, s)

Endothermic peak top temperature in DSC: 202° C.
Elemental analysis: C$_7$H$_{14}$N$_2$.C$_4$H$_4$O$_4$
Theoretical value: C, 54.53%, H, 7.49%, N, 11.56%
Actual measured value: C, 54.4%, H, 7.5%, N, 11.7%

Example 10: Synthesis of (R)-3-aminoquinuclidine.monoterephthalate

Methanol suspension (35.21 g) containing terephthalic acid (5.26 g: 31.7 mmol) was charged into a 50 mL-flask equipped with a mechanical stirrer, a thermometer, and a cooling line, and methanol solution (12.08 g) containing (R)-3-aminoquinuclidine (4.05 g: 32.1 mmol) was added thereto while stirring at room temperature. Precipitated crystals were filtered, and then dried under reduced pressure at 60° C., to obtain (R)-3-aminoquinuclidine.monoterephthalate (8.12 g: 27.7 mmol, yield=87%) as a white crystal.

1H-NMR (D$_2$O, ppm): 1.77-1.98 (4H, m), 2.22-2.27 (1H, m), 3.05-3.26 (5H, m), 3.59-3.65 (1H, m), 3.72-3.76 (1H, m), 7.72 (4H, s)

Endothermic peak top temperature in DSC: 250° C.
Elemental analysis: C$_7$H$_{14}$N$_2$.C$_8$H$_6$O$_4$
Theoretical value: C, 61.63%, H, 6.90%, N, 9.58%
Actual measured value: C, 61.6%, H, 6.7%, N, 9.2%

Example 11: Synthesis of (R)-3-aminoquinuclidine.monooxalate

Ethanol solution (14.86 g) containing oxalic acid (2.86 g: 31.8 mmol) was charged into a 50 mL-flask equipped with a mechanical stirrer, a thermometer, and a cooling line, and ethanol solution (12 g) containing (R)-3-aminoquinuclidine (4.00 g: 31.7 mmol) was added thereto while stirring at room temperature. Precipitated crystals were filtered, and then dried under reduced pressure at 60° C., to obtain (R)-3-aminoquinuclidine.monooxalate (3.14 g: 14.5 mmol, yield=46%) as a white crystal.

1H-NMR (D$_2$O, ppm): 1.84-2.02 (4H, m), 2.28-2.31 (1H, m), 3.10-3.27 (5H, m), 3.63-3.69 (1H, m), 3.77-3.81 (1H, m)

Endothermic peak top temperature in DSC: 282° C.
Elemental analysis: C$_7$H$_{14}$N$_2$.C$_2$H$_2$O$_4$
Theoretical value: C, 49.99%, H, 7.46%, N, 12.96%
Actual measured value: C, 50.1%, H, 7.4%, N, 13.1%

Example 12: Synthesis of (R)-3-aminoquinuclidine.mono-p-toluenesulfonate

Isopropanol solution (31.02 g) containing p-toluenesulfonic acid monohydrate (6.02 g: 31.6 mmol) was charged into a 100 mL-flask equipped with a mechanical stirrer, a thermometer, and a cooling line, and isopropanol solution (12.02 g) containing (R)-3-aminoquinuclidine (4.01 g: 31.8 mmol) was added thereto while stirring at room temperature. Precipitated crystals were filtered, and then dried under reduced pressure at 60° C., to obtain (R)-3-aminoquinuclidine.mono-p-toluenesulfonate (9.02 g: 30.2 mmol, yield=95%) as a white crystal.

1H-NMR (D$_2$O, ppm): 1.62-1.99 (5H, m), 2.25 (3H, s), 2.65-2.70 (1H, m), 2.94-3.13 (4H, m), 3.21-3.26 (1H, m), 3.35-3.41 (1H, m), 7.22 (2H, d, J=8 Hz), 7.54 (2H, d, J=8 Hz)

Endothermic peak top temperature in DSC: 221° C.
Elemental analysis: C$_7$H$_{14}$N$_2$.C$_7$H$_8$O$_3$S
Theoretical value: C, 56.35%, H, 7.43%, N, 9.39%, S 10.74%
Actual measured value: C, 56.3%, H, 7.4%, N, 9.5%, S 10.3%

Example 13: Synthesis of (R)-3-aminoquinuclidine.mono-(−)-10-camphorsulfonate Isopropanol solution (25.73 g) containing (−)-10-camphorsulfonic acid (5.51 g: 23.7 mmol) was charged into a 50 mL-flask equipped with a mechanical stirrer, a thermometer, and a cooling line, and isopropanol solution (9.01 g) containing (R)-3-aminoquinuclidine (2.99 g: 23.7 mmol) was added thereto while stirring at room temperature. Precipitated crystals were filtered, and then dried under reduced pressure at 60° C., to obtain (R)-3-aminoquinuclidine.mono-(−)-10-camphorsulfonate (7.85 g: 21.9 mmol, yield=92%) as a white crystal.

1H-NMR (D₂O, ppm): 0.68 (3H, s), 0.89 (3H, s), 1.27-1.34 (1H, m), 1.46-1.53 (1H, m), 1.64-2.02 (8H, m), 2.22-2.31 (2H, m), 2.65-2.72 (1H, m), 2.72 (1H, d, J=15.3 Hz), 2.95-3.13 (4H, m), 3.13 (1H, d, J=15.3 Hz), 3.22-3.29 (1H, m), 3.37-3.43 (1H, m)

Endothermic peak top temperature in DSC: 201° C.

Elemental analysis: $C_7H_{14}N_2C_{10}H_{16}O_4S$

Theoretical value: C, 56.96%, H, 8.44%, N, 7.81%, S 8.94%

Actual measured value: C, 56.9%, H, 8.3%, N, 7.8%, S 8.6%

Comparative Example 10: Synthesis of (R)-3-aminoquinuclidine-dihydrobromide

Isopropanol solution (30.11 g) containing (R)-3-aminoquinuclidine (4.94 g: 39.1 mmol) was charged into a 50 mL-flask equipped with a mechanical stirrer, a thermometer, and a cooling line, and 47% hydrobromic acid (13.64 g: 79.2 mmol) was added thereto while stirring at room temperature. Precipitated crystals were filtered, and then dried under reduced pressure at 60° C., to obtain (R)-3-aminoquinuclidine-dihydrobromide (6.73 g: 23.4 mmol, yield=60%) as a white crystal.

1H-NMR (D₂O, ppm): 1.88-2.06 (4H, m), 2.32-2.35 (1H, m), 3.14-3.33 (5H, m), 3.68-3.74 (1H, m), 3.82-3.85 (1H, m)

Endothermic peak top temperature in DSC: 274° C.

Comparative Example 11: Synthesis of (R)-3-aminoquinuclidine.dinitrate

Isopropanol solution (39.10 g) containing (R)-3-aminoquinuclidine (3.98 g: 31.5 mmol) was charged into a 100 mL-flask equipped with a mechanical stirrer, a thermometer, and a cooling line, and 70% nitric acid (5.91 g: 64.7 mmol) was added thereto while stirring at room temperature. Precipitated crystals were filtered, and then dried under reduced pressure at 60° C., to obtain (R)-3-aminoquinuclidine.dinitrate (7.40 g: 29.3 mmol, yield=93%) as a white crystal.

1H-NMR (D₂O, ppm): 1.88-2.05 (4H, m), 2.31-2.34 (1H, m), 3.13-3.31 (5H, m), 3.67-3.73 (1H, m), 3.80-3.83 (1H, m)

Endothermic peak top temperature in DSC: 141° C.

Comparative Example 12: Synthesis of (R)-3-aminoquinuclidine.diacetate

Isopropanol solution (30.16 g) containing (R)-3-aminoquinuclidine (5.03 g: 39.9 mmol) was charged into a 50 mL-flask equipped with a mechanical stirrer, a thermometer, and a cooling line, and acetic acid (4.75 g: 79.1 mmol) was added thereto while stirring at room temperature. Precipitated crystals were filtered, and then dried under reduced pressure at 60° C., to obtain (R)-3-aminoquinuclidine-diacetate (4.41 g: 17.9 mmol, yield=45%) as a white crystal.

1H-NMR (D₂O, ppm): 1.75 (6H, s), 1.82-2.01 (4H, m), 2.23-2.27 (1H, m), 3.06-3.26 (5H, m), 3.60-3.66 (1H, m), 3.70-3.75 (1H, m)

Endothermic peak top temperature in DSC: 105° C., 135° C.

Comparative Example 13: Synthesis of (R)-3-aminoquinuclidine.monopropionate

Toluene solution (24.03 g) containing (R)-3-aminoquinuclidine (3.99 g: 31.6 mmol) was charged into a 50 mL-flask equipped with a mechanical stirrer, a thermometer, and a cooling line, and propionic acid (2.36 g: 31.9 mmol) was added thereto while stirring at room temperature. Precipitated crystals were filtered, and then dried under reduced pressure at 60° C., to obtain (R)-3-aminoquinuclidine-monopropionate (3.30 g: 16.5 mmol, yield=52%) as a white crystal.

1H-NMR (D₂O, ppm): 0.89 (3H, t, J=7.8 Hz), 1.63-1.99 (4H, m), 2.01 (2H, q, J=7.8 Hz), 2.65-2.69 (1H, m), 2.93-3.08 (5H, m), 3.22-3.26 (1H, m), 3.35-3.41 (1H, m)

Endothermic peak top temperature in DSC: 116° C., 149° C.

Comparative Example 14: Synthesis of (R)-3-aminoquinuclidine.dibenzoate

Isopropanol solution (20.03 g) containing (R)-3-aminoquinuclidine (5.05 g: 40.0 mmol) was charged into a 50 mL-flask equipped with a mechanical stirrer, a thermometer, and a cooling line, and isopropanol solution (24.87 g) containing benzoic acid (9.70 g: 79.4 mmol) was added thereto while stirring at room temperature. Precipitated crystals were filtered, and then dried under reduced pressure at 60° C., to obtain (R)-3-aminoquinuclidine.dibenzoate (9.54 g: 25.8 mmol, yield=64%) as a white crystal.

1H-NMR (D₂O, ppm): 1.79-1.98 (4H, m), 2.23-2.27 (1H, m), 3.06-3.26 (5H, m), 3.59-3.66 (1H, m), 3.71-3.76 (1H, m), 7.29-7.34 (4H, m), 7.37-7.41 (2H, m), 7.70-7.72 (4H, m)

Endothermic peak top temperature in DSC: 126° C., 218° C.

Comparative Example 15: Synthesis of (R)-3-aminoquinuclidine.monomaleate

Methanol solution (14.08 g) containing (R)-3-aminoquinuclidine (4.04 g: 32.0 mmol) was charged into a 50 mL-flask equipped with a mechanical stirrer, a thermometer, and a cooling line, and methanol solution (13.70 g) containing maleic acid (3.69 g: 31.8 mmol) was added thereto while stirring at room temperature. Further, isopropanol (16.02 g) was added thereto, and precipitated crystals were filtered, and then dried under reduced pressure at 60° C., to obtain (R)-3-aminoquinuclidine-monomaleate (5.90 g: 24.4 mmol, yield=76%) as a white crystal.

1H-NMR (D₂O, ppm): 1.83-2.02 (4H, m), 2.24-2.28 (1H, m), 3.08-3.29 (5H, m), 3.60-3.66 (1H, m), 3.71-3.75 (1H, m) 5.91 (2H, s)

Endothermic peak top temperature in DSC: 159° C., 188° C.

Comparative Example 16: Synthesis of (R)-3-aminoquinuclidine.2/3citrate

Isopropanol solution (25.00 g) containing (R)-3-aminoquinuclidine (5.01 g: 39.7 mmol) was charged into a 50 mL-flask equipped with a mechanical stirrer, a thermometer, and a cooling line, and isopropanol solution (15.54 g) containing citric acid monohydrate (5.57 g: 26.5 mmol) was added thereto while stirring at room temperature. Precipitated crystals were filtered, and then dried under reduced pressure at 60° C., to obtain (R)-3-aminoquinuclidine.2/3citrate (8.56 g: 33.7 mmol, yield=85%) as a white crystal.

1H-NMR (D₂O, ppm): 1.01-2.03 (4H, m), 2.27-2.31 (1H, m), 2.41 (4/3H, d, J=15.3 Hz), 2.53 (4/3H, d, J=15.3 Hz), 3.10-3.31 (5H, m), 3.61-3.68 (1H, m), 3.76-3.80 (1H, m)

Endothermic peak top temperature in DSC: 195° C.

Comparative Example 17: Synthesis of (R)-3-aminoquinuclidine.monomesylate

Isopropanol solution (36.25 g) containing (R)-3-aminoquinuclidine (4.19 g: 33.2 mmol) was charged into a 100 mL-flask equipped with a mechanical stirrer, a thermometer, and a cooling line, and mesylic acid (3.19 g: 33.2 mmol) was added thereto while stirring at room temperature. Precipitated crystals were filtered, and then dried under reduced pressure at 60° C., to obtain (R)-3-aminoquinuclidine.monomesylate (7.06 g: 31.7 mmol, yield=96%) as a white crystal.

1H-NMR (D$_2$O, ppm): 1.64-2.00 (5H, m), 2.66 (3H, s), 2.67-2.71 (1H, m), 2.95-3.14 (4H, m), 3.24-3.28 (1H, m), 3.37-3.43 (1H, m)

Endothermic peak top temperature in DSC: 181° C.

Experimental Example 2: Deliquescence Test

The acid addition salts (about 0.5 g) of (R)-3-aminoquinuclidine obtained in Examples 7 to 13, Referential Example 2, and Comparative Examples 10 to 17 were allowed to stand for 1 hour, under the conditions of 24 to 25° C. and a humidity of 74 to 76%, and a deliquescence was observed by a visual evaluation. The results are shown in Table 2.

TABLE 2

| | Salt | Deliquescence |
|---|---|---|
| Example 7 | Sesquiphosphate | Not deliquesce |
| Example 8 | Monosulfate | Not deliquesce |
| Example 9 | Monofumarate | Not deliquesce |
| Example 10 | Monoterephthalate | Not deliquesce |
| Example 11 | Monooxalate | Not deliquesce |
| Example 12 | Mono-p-toluenesulfonate | Not deliquesce |
| Example 13 | Mono-(−)-10-camphorsulfonate | Not deliquesce |
| Referential Example 2 | Dihydrochlorid | Immediately deliquesce |
| Comparative Example 10 | Dihydrobromide | Gradually deliquesce |
| Comparative Example 11 | Dinitrate | Gradually deliquesce |
| Comparative Example 12 | Diacetate | Immediately deliquesce |
| Comparative Example 13 | Monopropionate | Immediately deliquesce |
| Comparative Example 14 | Dibenzoate | Immediately deliquesce |
| Comparative Example 15 | Monomaleate | Gradually deliquesce |
| Comparative Example 16 | ⅔ citrate | Immediately deliquesce |
| Comparative Example 17 | Monomesylate | Gradually deliquesce |

Referential Example 4: Synthesis of (S)-3-aminoquinuclidine.dihydrochloride (S)-3-aminoquinuclidine.dihydrochloride was obtained by subjecting a starting material i.e., 3-quinuclidinone.monohydrochloride to some sequential reactions in accordance with a method described in Synth. Commun., 22 (13), 1895-1911 (1992).

Referential Example 5: Synthesis of (S)-3-aminoquinuclidine (S)-3-aminoquinuclidine was obtained by neutralization-extracting (S)-3-aminoquinuclidine dihydrochloride and concentrating the same in accordance with a method described in Japanese Patent No. 4779248.

Example 14: Synthesis of (S)-3-aminoquinuclidine.sesquiphosphate

Methanol solution (27.15 g) containing (S)-3-aminoquinuclidine (3.17 g: 25.1 mmol) was charged into a 50 mL-flask equipped with a mechanical stirrer, a thermometer, and a cooling line, and phosphoric acid (85% in water) (4.34 g: 37.6 mmol) was added thereto while stirring at room temperature. Precipitated crystals were filtered, and then dried under reduced pressure at 60° C., to obtain (S)-3-aminoquinuclidine sesquiphosphate (6.90 g: 25.3 mmol, yield=101%) as a white crystal.

1H-NMR (D$_2$O, ppm): 1.81-2.00 (4H, m), 2.23-2.27 (1H, m), 3.06-3.27 (5H, m), 3.59-3.66 (1H, m), 3.71-3.75 (1H, m)

Endothermic peak top temperature in DSC: 192° C., 230° C., 280° C.

Elemental analysis: $C_7H_{14}N_2 \cdot 1.5H_3PO_4$

Theoretical value: P, 17.01%

Actual measured value: P, 17.3%

Example 15: Synthesis of (S)-3-aminoquinuclidine.monosulfate

Toluene solution (33.99 g) containing (S)-3-aminoquinuclidine (4.05 g: 32.1 mmol) was charged into a 50 mL-flask equipped with a mechanical stirrer, a thermometer, and a cooling line, and 95% sulfuric acid (3.32 g: 32.2 mmol) was added thereto while stirring on ice. Precipitated crystals were filtered, and then dried under reduced pressure at 60° C., to obtain (S)-3-aminoquinuclidine.monosulfate (6.12 g (27.3 mmol, yield=85%) as a white crystal.

1H-NMR (D$_2$O, ppm): 1.85-2.03 (4H, m), 2.30-2.34 (1H, m), 3.11-3.34 (5H, m), 3.66-3.72 (1H, m), 3.79-3.84 (1H, m)

Endothermic peak top temperature in DSC: 86° C., 188° C., 297° C.

Elemental analysis: $C_7H_{14}N_2 \cdot H_2SO_4$

Theoretical value: C, 37.49%, H, 7.19%, N, 12.49%, S 14.29%

Actual measured value: C, 36.6%, H, 7.1%, N, 12.2%, S 14.2%

Example 16: Synthesis of (S)-3-aminoquinuclidine.monofumarate

Methanol suspension (20.86 g) containing fumaric acid (2.76 g:23.8 mmol) was charged into a 50 mL-flask equipped with a mechanical stirrer, a thermometer, and a cooling line, and methanol solution (9.02 g) containing (S)-3-aminoquinuclidine (3.01 g: 23.9 mmol) was added thereto while stirring at room temperature. Precipitated crystals were filtered, and then dried under reduced pressure at 60° C., to obtain (S)-3-aminoquinuclidine.monofumarate (5.40 g: 22.3 mmol, yield=93%) as a white crystal.

1H-NMR (D$_2$O, ppm): 1.83-2.02 (4H, m), 2.27-2.30 (1H, m), 3.10-3.28 (5H, m), 3.62-3.69 (1H, m) 3.76-3.81 (1H, m), 6.36 (2H, s)

Endothermic peak top temperature in DSC: 201° C.

Elemental analysis: $C_7H_{14}N_2 \cdot C_4H_4O_4$

Theoretical value: C, 54.53%, H, 7.49%, N, 11.56%

Actual measured value: C, 54.5%, H, 7.4%, N, 11.7%

Example 17: Synthesis of (S)-3-aminoquinuclidine.monoterephthalate

Methanol suspension (21.91 g) containing terephthalic acid (3.90 g: 23.5 mmol) was charged into a 50 mL-flask equipped with a mechanical stirrer, a thermometer, and a cooling line, and methanol solution (9.02 g) containing (S)-3-aminoquinuclidine (3.00 g: 23.8 mmol) was added thereto while stirring at room temperature. Precipitated crystals were filtered, and then dried under reduced pressure at 60° C., to obtain (S)-3-aminoquinuclidine.monoterephthalate (5.96 g: 20.3 mmol, yield=86%) as a white crystal.

1H-NMR (D$_2$O, ppm): 1.77-1.97 (4H, m), 2.21-2.25 (1H, m), 3.04-3.26 (5H, m), 3.58-3.65 (1H, m), 3.70-3.75 (1H, m), 7.71 (4H, s)

Endothermic peak top temperature in DSC: 251° C.
Elemental analysis: C$_7$H$_{14}$N$_2$.C$_8$H$_6$O$_4$
Theoretical value: C, 61.63%, H, 6.90%, N, 9.58%
Actual measured value: C, 61.4%, H, 6.7%, N, 9.0%

Example 18: Synthesis of (S)-3-aminoquinuclidine.monooxalate

Methanol solution (24.20 g) containing (S)-3-aminoquinuclidine (4.20 g: 33.3 mmol) was charged into a 50 mL-flask equipped with a mechanical stirrer, a thermometer, and a cooling line, and methanol solution (11.01 g) containing oxalic acid (3.00 g: 33.3 mmol) was added thereto while stirring at room temperature. Precipitated crystals were filtered, and then dried under reduced pressure at 60° C., to obtain (S)-3-aminoquinuclidine.monooxalate (6.20 g: 28.7 mmol, yield=86%) as a white crystal.

1H-NMR (D$_2$O, ppm): 1.85-2.02 (4H, m) 2.28-2.31 (1H, m) 3.11-3.27 (5H, m), 3.63-3.69 (1H, m), 3.77-3.81 (1H, m)

Endothermic peak top temperature in DSC: 283° C.
Elemental analysis: C$_7$H$_{14}$N$_2$.C$_2$H$_2$O$_4$
Theoretical value: C, 49.99%, H, 7.46%, N, 12.96%
Actual measured value: C, 50.0%, H, 7.4%, N, 13.0%

Example 19: Synthesis of (S)-3-aminoquinuclidine.mono-p-toluenesulfonate 2-propanol solution (22.68 g) containing p-toluenesulfonic acid monohydrate (4.55 g: 23.9 mmol) was charged into a 50 mL-flask equipped with a mechanical stirrer, a thermometer, and a cooling line, and 2-propanol solution (10.52 g) containing (S)-3-aminoquinuclidine (3.00 g: 23.8 mmol) was added thereto while stirring at room temperature. Precipitated crystals were filtered, and then dried under reduced pressure at 60° C., to obtain (S)-3-aminoquinuclidine.mono-p-toluenesulfonate (6.87 g: 23.0 mmol, yield=97%) as a white crystal.

1H-NMR (D$_2$O, ppm): 1.61-1.98 (5H, m), 2.24 (3H, s), 2.64-2.69 (1H, m), 2.92-3.11 (4H, m), 3.20-3.25 (1H, m), 3.34-3.40 (1H, m), 7.22 (2H, d, J=8.2 Hz), 7.54 (2H, d, J=8.2 Hz)

Endothermic peak top temperature in DSC: 220° C.
Elemental analysis: C$_7$H$_{14}$N$_2$.C$_7$H$_8$O$_3$S
Theoretical value: C, 56.35%, H, 7.43%, N, 9.39%, S 10.74%
Actual measured value: C, 56.3%, H, 7.4%, N, 9.5%, S 10.3%

Comparative Example 18: Synthesis of (S)-3-aminoquinuclidine.dinitrate 2-propanol solution (23.73 g) containing (S)-3-aminoquinuclidine (2.93 g: 23.2 mmol) was charged into a 50 mL-flask equipped with a mechanical stirrer, a thermometer, and a cooling line, and 70% nitric acid (4.31 g: 47.2 mmol) was added thereto while stirring at room temperature. Precipitated crystals were filtered, and then dried under reduced pressure at 60° C., to obtain (S)-3-aminoquinuclidine.dinitrate (5.71 g: 22.6 mmol, yield=98%) as a white crystal.

1H-NMR (D$_2$O, ppm): 1.84-2.04 (4H, m), 2.29-2.33 (1H, m), 3.11-3.30 (5H, m), 3.65-3.71 (1H, m), 3.79-3.84 (1H, m)

Endothermic peak top temperature in DSC: 140° C.

Comparative Example 19: Synthesis of (S)-3-aminoquinuclidine.diacetate

Toluene solution (28.22 g) containing (S)-3-aminoquinuclidine (3.03 g: 24.0 mmol) was charged into a 50 mL-flask equipped with a mechanical stirrer, a thermometer, and a cooling line, and acetic acid (2.86 g: 47.6 mmol) was added thereto while stirring at room temperature. Precipitated crystals were filtered, and then dried under reduced pressure at 60° C., to obtain (S)-3-aminoquinuclidine.diacetate (5.02 g: 20.4 mmol, yield=85%) as a white crystal.

1H-NMR (D$_2$O, ppm): 1.74 (6H, s), 1.76-2.01 (4H, m), 2.22-2.26 (1H, m), 3.06-3.26 (5H, m), 3.59-3.65 (1H, m), 3.69-3.73 (1H, m)

Endothermic peak top temperature in DSC: 103° C., 135° C.

Experimental Example 3: Deliquescence Test

The acid addition salts (about 0.5 g) of (S)-3-aminoquinuclidine obtained in Examples 14 to 19, and Comparative Examples 18 to 19 were allowed to stand for 1 hour, under the conditions of 24 to 26° C., and a humidity of 75 to 78%, and a deliquescence was observed by a visual evaluation. The results are shown in Table 3.

TABLE 3

| | Salt | Deliquescence |
|---|---|---|
| Example 14 | Sesquiphosphate | Not deliquesce |
| Example 15 | Monosulfate | Not deliquesce |
| Example 16 | Monofumarate | Not deliquesce |
| Example 17 | Monoterephthalate | Not deliquesce |
| Example 18 | Monooxalate | Not deliquesce |
| Example 19 | Mono-p-toluenesulfonate | Not deliquesce |
| Referential Example 4 | Dihydrochlorid | Immediately deliquesce |
| Comparative Example 18 | Dinitrate | Gradually deliquesce |
| Comparative Example 19 | Diacetate | Immediately deliquesce |

Although the present invention has been described with reference to specific embodiments, various changes and modifications obvious to those skilled in the art are possible without departing from the scope of the appended claims.

What is claimed is:

1. An acid addition salt selected from the group consisting of:
   [1] racemic 3-aminoquinuclidine.sesquiphosphate,
   [2] racemic 3-aminoquinuclidine.monofumarate,
   [3] racemic 3-aminoquinuclidine.monoterephthalate,
   [4] racemic 3-aminoquinuclidine.monooxalate,
   [5] racemic 3-aminoquinuclidine.mono-p-toluenesulfonate, and
   [6] racemic 3-aminoquinuclidine.mono-(±)-10-camphorsulfonate;
   wherein the acid addition salt does not exhibit deliquescence.

2. An acid addition salt selected from the group consisting of:
   [1] (R)-3-aminoquinuclidine.sesquiphosphate,
   [2] (R)-3-aminoquinuclidine.monosulfate,
   [3] (R)-3-aminoquinuclidine.monofumarate,
   [4] (R)-3-aminoquinuclidine.monoterephthalate,
   [5] (R)-3-aminoquinuclidine.monooxalate,

[6] (R)-3-aminoquinuclidine.mono-p-toluenesulfonate, and
[7] (R)-3-aminoquinuclidine.mono-(−)-10-camphorsulfonate;
wherein the acid addition salt does not exhibit deliquescence.

3. An acid addition salt selected from the group consisting of:
[1] (S)-3-aminoquinuclidine.sesquiphosphate,
[2] (S)-3-aminoquinuclidine.monosulfate,
[3] (S)-3-aminoquinuclidine.monofumarate,
[4] (S)-3-aminoquinuclidine.monoterephthalate,
[5] (S)-3-aminoquinuclidine.monooxalate, and
[6] (S)-3-aminoquinuclidine.mono-p-toluenesulfonate;
wherein the acid addition salt does not exhibit deliquescence.

* * * * *